US009149609B2

(12) United States Patent
Ansel et al.

(10) Patent No.: US 9,149,609 B2
(45) Date of Patent: Oct. 6, 2015

(54) CATHETER FOR REMOVAL OF AN ORGANIZED EMBOLIC THROMBUS

(75) Inventors: Gary M. Ansel, Columbus, OH (US); Michael J. Bonnette, Minneapolis, MN (US); Eric J. Thor, Arden Hills, MN (US); David B. Morris, Anoka, MN (US); Stephen E. Weisel, Brook Park, MN (US)

(73) Assignee: Embolitech, LLC, Austin, TX (US)

( * ) Notice: Subject to any disclaimer, the term of this patent is extended or adjusted under 35 U.S.C. 154(b) by 1179 days.

(21) Appl. No.: 12/152,367

(22) Filed: May 14, 2008

(65) Prior Publication Data

US 2008/0312681 A1    Dec. 18, 2008

Related U.S. Application Data

(60) Provisional application No. 60/934,268, filed on Jun. 12, 2007.

(51) Int. Cl.
*A61M 29/00* (2006.01)
*A61M 25/06* (2006.01)
(Continued)

(52) U.S. Cl.
CPC .......... *A61M 25/0662* (2013.01); *A61B 17/221* (2013.01); *A61B 17/22031* (2013.01);
(Continued)

(58) Field of Classification Search
CPC ............... A61B 17/22031; A61B 2017/22034; A61B 2017/22035; A61B 17/221; A61B 2017/22044; A61B 2017/22067; A61B 2017/22094; A61B 2025/0175
USPC ................................................. 606/108, 200
See application file for complete search history.

(56) References Cited

U.S. PATENT DOCUMENTS 4,425,908 A    1/1984  Simon
4,611,594 A *  9/1986  Grayhack et al. .............. 606/127
(Continued)

FOREIGN PATENT DOCUMENTS

EP    0655228    11/1994
EP    1545388    5/2009
(Continued)

OTHER PUBLICATIONS

Report on Patentability Dated Dec. 17, 2009 From Corresponding International Application PCT/US08/66644.
(Continued)

*Primary Examiner* — Katherine Rodjom
(74) *Attorney, Agent, or Firm* — DuBois, Bryant & Campbell LLP; William D. Wiese

(57) ABSTRACT

The general purpose of the present invention is to provide a catheter for removal of an organized embolic thrombus, preferably in conjunction with a distal occlusion balloon guidewire. The present invention consists of three main components including a capture/delivery sheath, a capture sleeve of mesh attached to a tube and a grasping mechanism attached to another tube which is central to the other components. Operative structures in the form of manifolds are connected to such components in order to manipulate and control the relative positions of the capture/delivery sheath, the capture sleeve and the grasping mechanism. An embolic thrombus is engaged by the deployable automatically expanding serrated fingers of a grasping mechanism in combination with a deployable automatically expanding mesh capture sleeve. The capture/delivery sheath is maneuvered to cause compression of the serrated fingers and of the mesh capture sleeve for subsequent removal of the embolic thrombus.

21 Claims, 15 Drawing Sheets

(51) Int. Cl.
*A61B 17/22* (2006.01)
*A61B 17/221* (2006.01)
A61B 17/00 (2006.01)
A61F 2/01 (2006.01)
A61M 25/00 (2006.01)
A61M 25/01 (2006.01)
A61M 25/10 (2013.01)

(52) U.S. Cl.
CPC ........... *A61B2017/00867* (2013.01); *A61B 2017/22044* (2013.01); *A61B 2017/22067* (2013.01); *A61B 2017/22094* (2013.01); *A61F 2002/011* (2013.01); *A61M 25/005* (2013.01); *A61M 2025/0175* (2013.01); *A61M 2025/1052* (2013.01)

(56) References Cited

U.S. PATENT DOCUMENTS

| | | | |
|---|---|---|---|
| 4,643,184 A | | 2/1987 | Mobin-Uddin |
| 4,690,672 A | | 9/1987 | Veltrup |
| 5,011,488 A | | 4/1991 | Ginsburg |
| 5,074,871 A | * | 12/1991 | Groshong ............... 606/170 |
| 5,102,415 A | | 4/1992 | Guenther et al. |
| 5,370,609 A | | 12/1994 | Drasler et al. |
| 5,688,234 A | * | 11/1997 | Frisbie ............... 604/22 |
| 5,785,675 A | | 7/1998 | Drasler et al. |
| 5,814,064 A | | 9/1998 | Daniel et al. |
| 5,908,435 A | * | 6/1999 | Samuels ............... 606/200 |
| 5,941,871 A | | 8/1999 | Adams et al. |
| 5,968,057 A | * | 10/1999 | Taheri ............... 606/159 |
| 5,971,938 A | | 10/1999 | Hart et al. |
| 5,989,271 A | | 11/1999 | Bonnette et al. |
| 6,001,118 A | | 12/1999 | Daniel et al. |
| 6,059,814 A | | 5/2000 | Ladd |
| 6,066,149 A | | 5/2000 | Samson et al. |
| 6,080,170 A | | 6/2000 | Nash et al. |
| 6,096,001 A | | 8/2000 | Drasler et al. |
| 6,135,977 A | | 10/2000 | Drasler et al. |
| 6,176,844 B1 | | 1/2001 | Lee |
| 6,203,561 B1 | | 3/2001 | Ramee et al. |
| 6,206,868 B1 | | 3/2001 | Parodi |
| 6,221,006 B1 | | 4/2001 | Dubrul et al. |
| 6,238,412 B1 | | 5/2001 | Dubrul et al. |
| 6,245,089 B1 | | 6/2001 | Daniel et al. |
| 6,258,061 B1 | | 7/2001 | Drasler et al. |
| 6,258,115 B1 | | 7/2001 | Dubrul et al. |
| 6,290,710 B1 | | 9/2001 | Cryer et al. |
| 6,325,815 B1 | | 12/2001 | Kusleika et al. |
| 6,325,816 B1 | | 12/2001 | Fulton, III et al. |
| 6,338,735 B1 | | 1/2002 | Stevens |
| 6,346,116 B1 | | 2/2002 | Brooks et al. |
| 6,361,546 B1 | | 3/2002 | Khosravi |
| 6,371,969 B1 | | 4/2002 | Tsugita et al. |
| 6,436,120 B1 | | 8/2002 | Meglin |
| 6,443,972 B1 | | 9/2002 | Bosma et al. |
| 6,447,531 B1 | | 9/2002 | Amplatz |
| 6,450,989 B2 | | 9/2002 | Dubrul et al. |
| 6,485,500 B1 | | 11/2002 | Kokish et al. |
| 6,485,502 B2 | | 11/2002 | Don Michael et al. |
| 6,491,660 B2 | | 12/2002 | Guo et al. |
| 6,511,492 B1 | | 1/2003 | Rosenbluth et al. |
| 6,517,551 B1 | * | 2/2003 | Driskill ............... 606/113 |
| 6,524,323 B1 | | 2/2003 | Nash et al. |
| 6,527,746 B1 | | 3/2003 | Oslund et al. |
| 6,544,209 B1 | | 4/2003 | Drasler et al. |
| 6,575,996 B1 | | 6/2003 | Denison et al. |
| 6,605,102 B1 | | 8/2003 | Mazzocchi et al. |
| 6,635,070 B2 | | 10/2003 | Leeflang et al. |
| 6,652,548 B2 | | 11/2003 | Evans et al. |
| 6,676,637 B1 | | 1/2004 | Bonnette et al. |
| 6,679,893 B1 | | 1/2004 | Tran |
| 6,682,546 B2 | | 1/2004 | Amplatz |
| 6,695,813 B1 | | 2/2004 | Boyle et al. |
| 6,695,858 B1 | | 2/2004 | Dubrul et al. |
| 6,712,835 B2 | | 3/2004 | Mazzocchi et al. |
| 6,726,701 B2 | | 4/2004 | Gilson et al. |
| 6,740,061 B1 | | 5/2004 | Oslund et al. |
| 6,758,855 B2 | | 7/2004 | Fulton, III et al. |
| 6,761,727 B1 | | 7/2004 | Ladd |
| 6,773,448 B2 | | 8/2004 | Kusleika et al. |
| 6,805,684 B2 | | 10/2004 | Bonnette et al. |
| 6,814,740 B2 | | 11/2004 | McAlister |
| 6,887,256 B2 | | 5/2005 | Gibson et al. |
| 6,989,019 B2 | | 1/2006 | Mazzocchi et al. |
| 7,011,654 B2 | | 3/2006 | Dubrul et al. |
| 7,163,550 B2 | | 1/2007 | Boismier |
| 7,169,154 B1 | * | 1/2007 | Que et al. ............... 606/127 |
| 7,241,304 B2 | | 7/2007 | Boyle et al. |
| 7,241,305 B2 | | 7/2007 | Ladd |
| 7,252,675 B2 | | 8/2007 | Denison et al. |
| 7,344,549 B2 | | 3/2008 | Boyle et al. |
| 7,491,210 B2 | | 2/2009 | Dubrul et al. |
| 7,537,601 B2 | | 5/2009 | Cano et al. |
| 7,717,936 B2 | | 5/2010 | Keating et al. |
| 7,766,936 B2 | | 8/2010 | Ladd |
| 7,780,694 B2 | | 8/2010 | Palmer et al. |
| 7,785,345 B2 | | 8/2010 | Ladd |
| 2002/0026203 A1 | * | 2/2002 | Bates et al. ............... 606/127 |
| 2002/0068954 A1 | * | 6/2002 | Foster ............... 606/200 |
| 2005/0119668 A1 | * | 6/2005 | Teague et al. ............... 606/127 |
| 2005/0192620 A1 | | 9/2005 | Cully et al. |
| 2006/0030877 A1 | | 2/2006 | Martinez et al. |
| 2006/0135987 A1 | * | 6/2006 | Jones et al. ............... 606/200 |
| 2006/0253145 A1 | * | 11/2006 | Lucas ............... 606/159 |
| 2007/0060942 A2 | | 3/2007 | Zadno-Azizi |
| 2007/0088383 A1 | | 4/2007 | Pal et al. |
| 2007/0191878 A1 | * | 8/2007 | Segner et al. ............... 606/200 |
| 2007/0208351 A1 | * | 9/2007 | Turner et al. ............... 606/108 |
| 2008/0234722 A1 | | 9/2008 | Bonnette et al. |

FOREIGN PATENT DOCUMENTS

| | | |
|---|---|---|
| FR | 2580504 | 10/1986 |
| FR | 2694687 | 2/1994 |
| JP | 8-187294 | 7/1996 |
| WO | 99/22673 | 5/1999 |
| WO | 01/15629 | 3/2001 |
| WO | 2008/036156 | 3/2008 |

OTHER PUBLICATIONS

Search Report Dated Aug. 26, 2006 From Corresponding EP Patent No. 1696966.
ALLIGATOR Retrieval Device (ARD), Chestnut Medical Technologies, Inc., Instructional Guide (www.chestnutmedical.com).
International Search Report Dated Dec. 12, 2009 From Corresponding International Application PCT/US08/66644.

* cited by examiner

CATHETER FOR REMOVAL OF AN ORGANIZED EMBOLIC THROMBUS

CROSS REFERENCES TO RELATED APPLICATIONS

This application claims priority from the earlier filed U.S. Provisional Application No. 60/934,268 filed Jun. 12, 2007, entitled "Catheter for Removal of Organized Embolic Thrombus", and is hereby incorporated into this application by reference as if fully set forth herein.

This patent application is related to patent application Ser. No. 11/581,613 filed on Oct. 16, 2006, entitled "Occlusive Guidewire System Having an Ergonomic Handheld Control Mechanism Prepackaged in a Pressurized Gaseous Environment and a Compatible Prepackaged Torqueable Kink-Resistant Guidewire With Distal Occlusive Balloon", which is pending. The prior application is hereby incorporated into this application by reference as if fully set forth herein.

BACKGROUND OF THE INVENTION

1. Field of the Invention

Tough organized embolic thrombus found in the vasculature of the human body may evolve from various origins. A trial thrombus that forms and organizes over the course of days or weeks can dislodge and create an acute arterial blockage. Another example would be a patient with peripheral arterial disease with thrombus in various stages of organization. An intervention procedure could dislodge organized thrombotic debris. The challenge with this debris is that it can be large and difficult to remove with currently available interventional tools. Balloons can smash the debris against the vessel wall if it can be located. Alternatively, there is a class of patients with acute peripheral occlusions, which patients are often immediately referred to surgery for an embolectomy procedure (Fogarty balloon) since this is an efficacious means of addressing the occlusion. The purpose of this invention is to make a practical device to enable an interventional alternative to this surgical embolectomy procedure. The present invention used in conjunction with other interventional equipment is capable of removing a tough and organized embolic thrombus in an interventional procedure. The present invention describes an intravascular catheter and procedure used for purposes of removing an organized embolic thrombus. The catheter generally consists of a grasping mechanism, a mesh capture sleeve, a capture/delivery sheath and housings which catheter is used for relative positioning of the grasping mechanism, the mesh capture sleeve, and the capture/delivery sheath. The catheter of the present invention is delivered over a guidewire. Typically, the guidewire would have a distal occlusion balloon for purposes of drawing the embolic material to within the grasping mechanism.

2. Description of the Prior Art

Surgical embolectomy is a viable method of removing a tough embolic thrombus. However, this surgical procedure is more invasive than an interventional procedure. In general, reducing the invasiveness of the procedure reduces the associated complications. With respect to interventional alternatives, the methods can range from infusion catheters which drip fibrinolytics to balloon procedures which compress the debris against the vessel wall to aspiration with large guide catheters. The debris is generally too tough for removal by mechanical thrombectomy catheters. Fibrinolytic infusion is a viable technique but not guaranteed to be successful. In addition, fibrinolytics are associated with adverse complications such as bleeding or hemorrhagic stroke. With respect to compressing the debris with a balloon or stent, this technique includes deficiencies. First, the debris is not always easily found via fluoroscopy. Second, stenting a thrombus does not remove it from the body and just ballooning and compressing the material will not guarantee that the debris would not further embolize distally.

SUMMARY OF THE INVENTION

The general purpose of the present invention is to provide a catheter for removal of an organized embolic thrombus and method of use. The present invention consist of three main parts: (a) a capture/delivery sheath; (b) a capture sleeve of mesh attached to a tube; and (c) a grasping mechanism attached to another tube which is central to the other two components. Other structures in the form of manifolds attach to such tubes to control the relative positions of the a capture/delivery sheath, the capture sleeve, and the grasping mechanism. Preferably, the invention is used with a 0.014" distal occlusion balloon guidewire (Guard Dog®) of the previously referenced patent application Ser. No. 11/581,613 or with another suitable pulling device, such as by the inventors or others. The inflatable balloon of the distal occlusion balloon guidewire is advanced past the debris, the balloon is inflated, and the balloon is retracted toward the present invention (analogous to a Fogarty procedure except that a Fogarty procedure uses a surgical opening to withdraw the material). The present invention provides a procedure for the successful capture of the debris. The present invention is introduced into the vasculature to the site of embolic thrombus material, also referred to herein as debris, and then telescoped appropriately along the length of the invention. The capture sleeve is advanced and automatically deployed outwardly beyond the capture/delivery sheath. The grasping mechanism is advanced and automatically deployed outwardly beyond the capture sleeve. In the anticipated procedure, the balloon of the distal occlusion balloon guidewire is inflated and used to pull the debris into the outwardly deployed serrated fingers of the grasping mechanism. Both the serrated fingers of the grasping mechanism and the inflated balloon of the distal occlusion balloon guidewire are pulled into the capture sleeve. Then, the inflatable balloon of the distal occlusion balloon guidewire is either advanced out of the capture sleeve or deflated. At this point, the capture/delivery sheath is advanced over the capture sleeve and grasping mechanism to capture the embolic material therein. As the capture/delivery sheath is advanced, the embolic material (debris) is squeezed downwardly and forwardly past the serrated teeth of the fingers. The serrations help tear and reduce the embolic material to smaller pieces as it is finally contained within the fingers and capture sleeve when the capture/delivery sheath is deployed fully thereover. The capture sleeve and the grasping mechanism along with the captured embolic material is withdrawn proximally along the length of the capture/delivery sheath, whereupon the embolic material can be removed from the vasculature and detached from the grasping mechanism. Another capture sleeve and grasping mechanism can be introduced or the same capture sleeve and the grasping mechanism can be cleaned and reintroduced into the vasculature via the capture/delivery sheath if required.

According to one or more embodiments or illustrations of the present invention, there is provided a catheter for removal of an organized embolic thrombus which is telescopeable along the length thereof including a capture/delivery sheath attached to a capture/delivery sheath operator in the form of a manifold, a capture sleeve of preformed memory shape mesh and attached capture sleeve positioning tube and capture sleeve operator in the form of a manifold, and a grasping mechanism having preformed memory shape serrated fingers and an attached grasping mechanism positioning tube and a grasping mechanism operator in the form of a manifold.

One significant aspect and feature of the present invention is the use of a catheter for the removal of an organized embolic thrombus during interventional procedures.

One significant aspect and feature of the present invention is the use of an organized embolic thrombus capture device which is preferably used in combination with a 0.014" distal occlusion balloon guidewire.

One significant aspect and feature of the present invention is the intention for use with a distal occlusion balloon, a distal filter or a distal cage on a guidewire for pulling debris to engage the present invention.

One significant aspect and feature of the present invention is the use of a catheter for the removal of an organized embolic thrombus, which catheter comprises a telescoping capture mechanism having (a) a capture/delivery sheath and a capture/delivery sheath operator; (b) a grasping mechanism, a grasping mechanism positioning tube and a grasping mechanism operator; and (c) a capture sleeve (mesh), a capture sleeve positioning tube and a capture sleeve operator.

One significant aspect and feature of the present invention is the use of a capture sleeve made from a nitinol and polyester mesh.

One significant aspect and feature of the present invention is the use of a thermal or laser source to stop the open end of the mesh capture sleeve (a nitinol/polymer weave) from fraying by melting the polymer ends thereof.

Another significant aspect and feature of the present invention is the use of nitinol for the grasping mechanism.

One significant aspect and feature of the present invention is the use of heat treated stainless steel for the grasping mechanism.

Another significant aspect and feature of the present invention is a grasping mechanism with two or more serrated fingers.

One significant aspect and feature of the present invention is a grasping mechanism operable within or extended from a mesh capture sleeve.

Yet another significant aspect and feature of the present invention is the use of a capture/delivery sheath for capturing an embolic thrombus or debris within a grasping mechanism and capture sleeve.

One significant aspect and feature of the present invention is the use of serrated fingers as the grasping mechanism in conjunction with the squeezing down and forward motion of a capture/delivery sheath in breaking up and reducing the size of the embolic debris, and wherein the serrations of the fingers act like teeth.

One significant aspect and feature of the present invention is the sequence in which the capture/delivery sheath, the grasping mechanism and a capture sleeve are used together in an optimal way of operating such a device.

An additional significant aspect and feature of the present invention is that using a $CO_2$ inflated balloon guidewire maximizes the internal space within the distal end of the invention available for debris capture since the gas inflated balloon guidewire occupies a small space.

Having thus briefly described one or more embodiments of the present invention, and having mentioned some significant aspects and features of the present invention, it is the principal object of the present invention to provide a catheter for removal of organized embolic thrombus and method of use.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
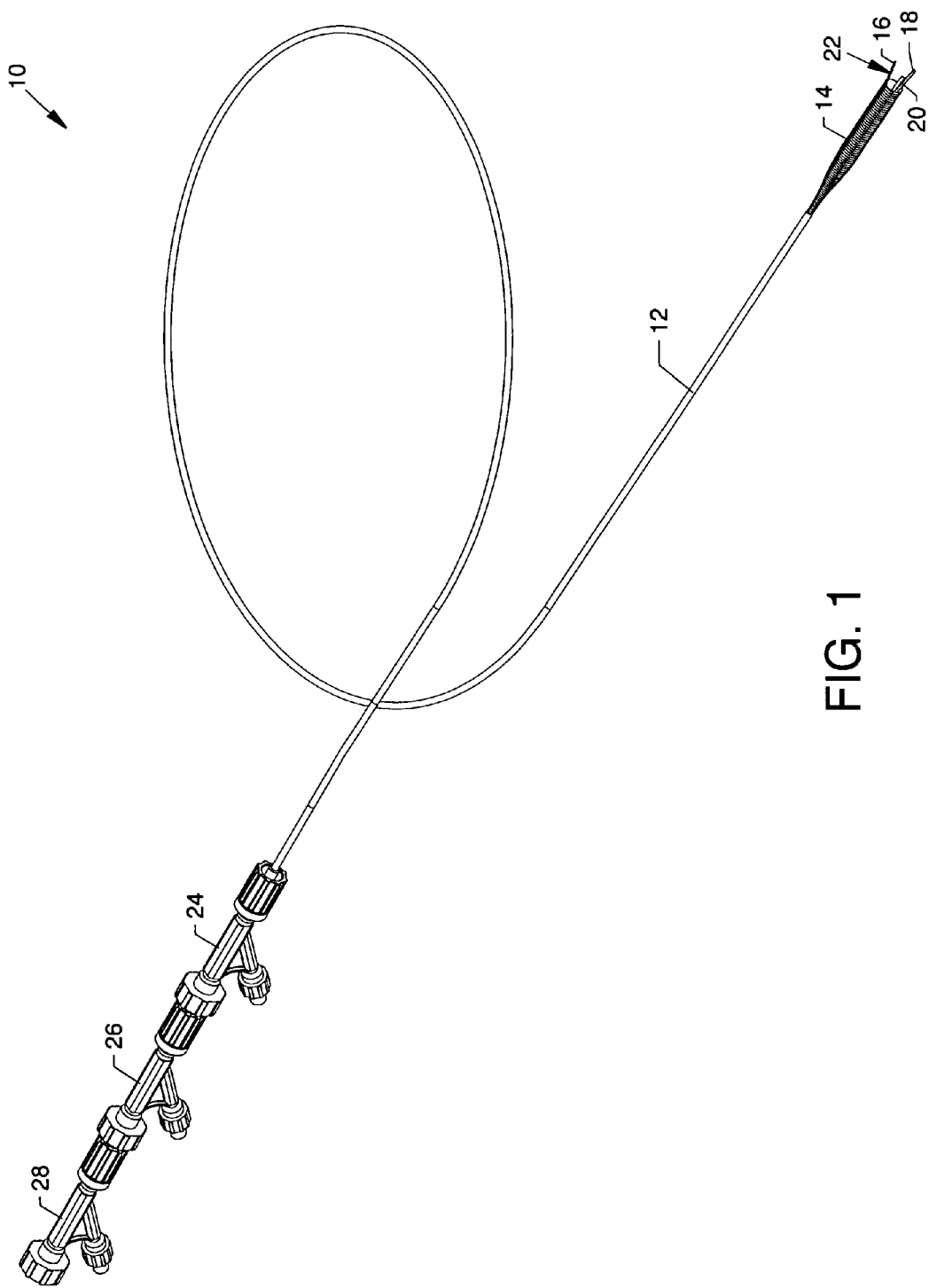
FIG. 1 is an isometric overview of the catheter for removal of an organized embolic thrombus, the present invention.

FIG. 1 is an isometric overview of the catheter 10 of the present invention for removal of an organized embolic thrombus. Fully or partially visible components of the present invention include a multiple function capture/delivery sheath 12, a distally located capture sleeve 14 shown in memory shape consisting of a nitinol and polymer mesh (shown in FIG. 3) extending distally from within the capture/delivery sheath 12, serrated fingers 16, 18 and 20 of a grasping mechanism 22 (FIG. 2) shown in memory shape, a capture/delivery sheath operator 24 in the form of a manifold attached to the proximal end of the capture/delivery sheath 12, a capture sleeve operator 26 in the form of a manifold in general longitudinal alignment with the capture/delivery sheath operator 24, and a grasping mechanism operator 28 in the form of a manifold in general longitudinal alignment with the capture sleeve operator 26.

Figure 2:
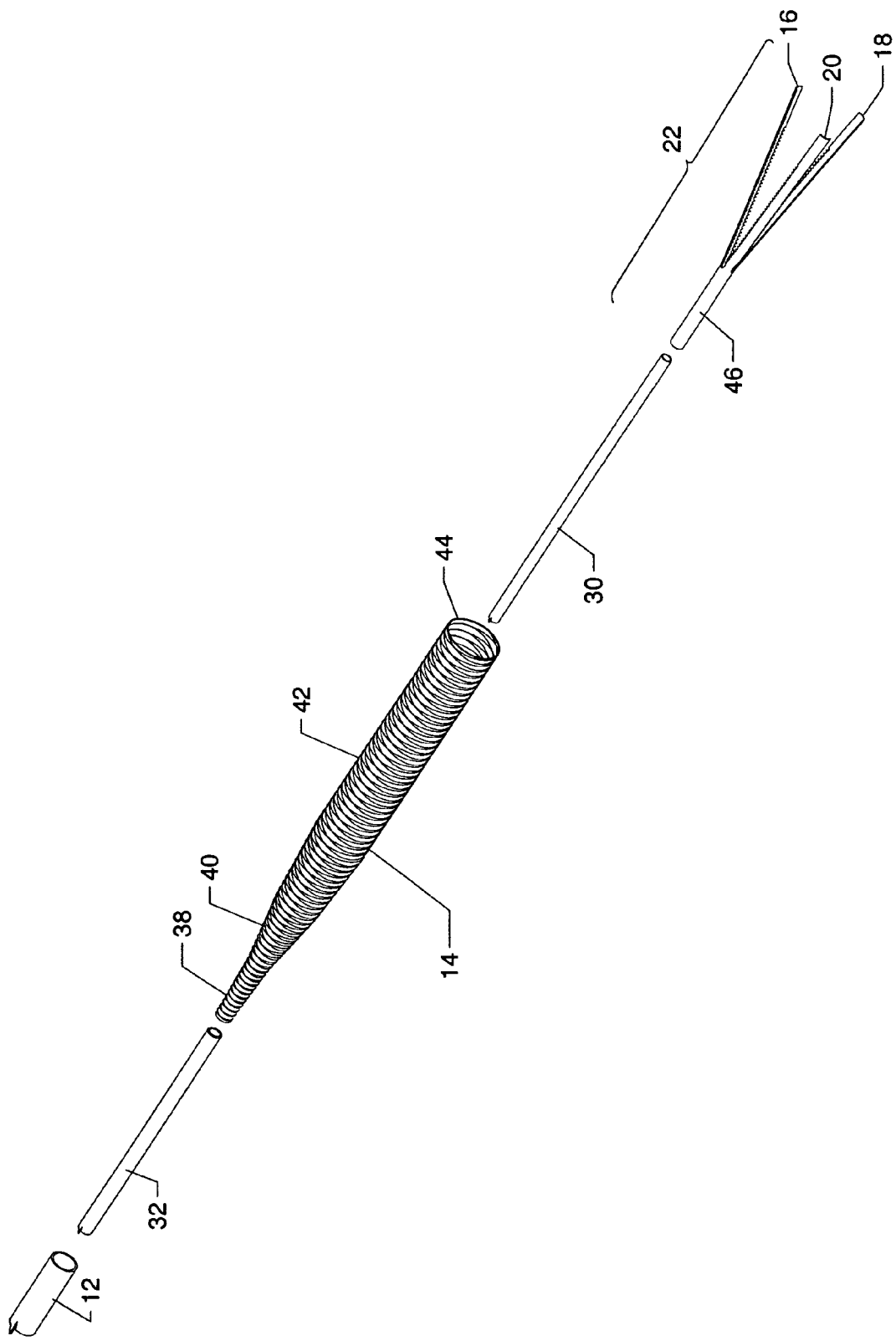
FIG. 2 is an exploded isometric view of the components located at the distal region of the invention.

FIG. 2 is an exploded isometric view of the components located at the distal region of the invention. The components maintain a coaxial relationship along and about the longitudinal axis of the invention consisting of inner, middle and outer components. The inner components consist of a grasping mechanism 22 having a memory shape preferably of nitinol or heat treated stainless steel and an attached grasping mechanism positioning tube 30 of braided polyimide or alternatively of flexible stainless steel, the middle components consist of the capture sleeve 14 and an attached capture sleeve positioning tube 32, and the outer component consists of a capture/delivery sheath 12 made of a flexible plastic material or some other suitable flexible material. The inner, middle and outer components maintain a coaxial relationship and are also attached to the capture/delivery sheath operator 24, the capture sleeve operator 26, and the grasping mechanism operator 28, respectively. More precisely, the grasping mechanism 22 is attached to the grasping mechanism operator 28 by the mutually attached grasping mechanism positioning tube 30; the capture sleeve 14 is attached to the capture sleeve operator 26 by a mutually attached capture sleeve positioning tube 32, and the capture/delivery sheath 12 is connected directly to the capture/delivery sheath operator 24.

Figure 3:
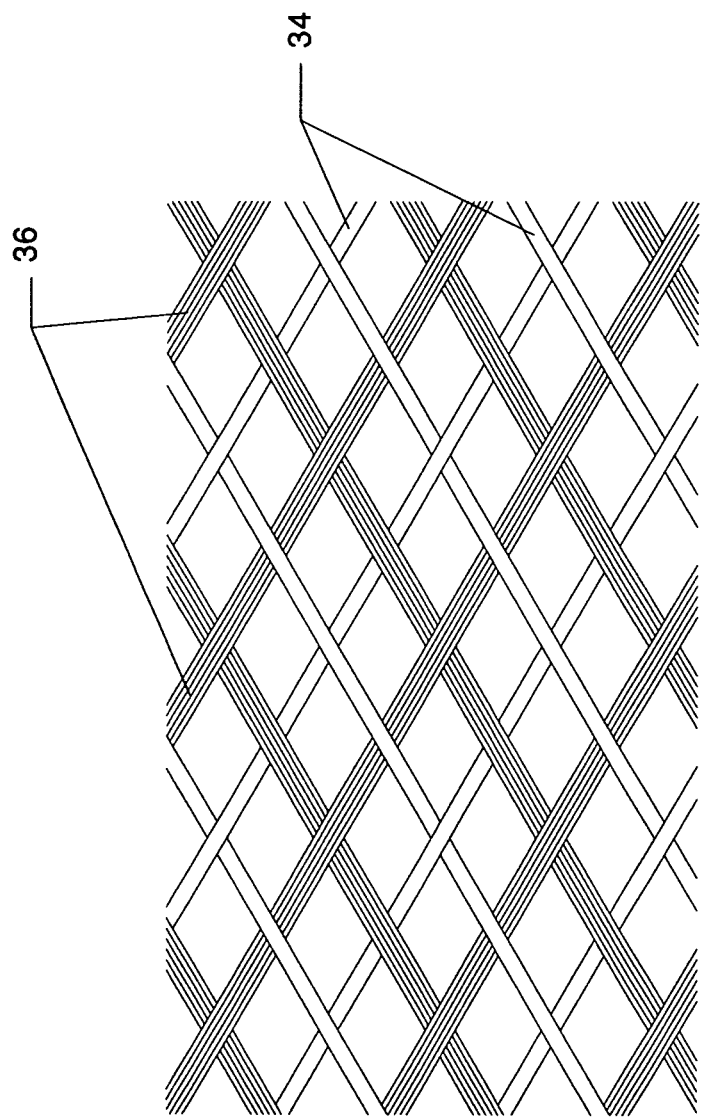
FIG. 3 illustrates a section of the woven mesh of a capture sleeve comprised of nitinol strands and multiple polymer strands.

The geometrically configured flexible capture sleeve 14 is generally tubular in shape and consists of a woven mesh preferably consisting of single nitinol strands 34 and multiple polymer strands 36, a representative section of which is shown in FIG. 3. All or a greater portion of the capture sleeve 14 is heat treated or otherwise treated to have an expanded memory shape. A constant diameter proximal section 38 of the capture sleeve 14 is attached to the distal end of the flexible capture sleeve positioning tube 32 of braided polyimide or alternatively of flexible stainless steel, by an adhesive, a weldment, or other suitable method. The capture sleeve 14 also includes a flared section 40 extending from the proximal section 38 and a tubular distal section 42 extending distally from the flared section 40 where such tubular distal section 42 can assume an expanded constant diameter or which may be conformal. The distal annular edge 44 of the capture sleeve 14 is prevented from fraying by melting the ends of the polymer strands 36 with a thermal or laser source or some other suitable method. The grasping mechanism 22 which can consist of nitinol, stainless steel or some other suitable material is also shown and further described in FIG. 4.

Figure 4:
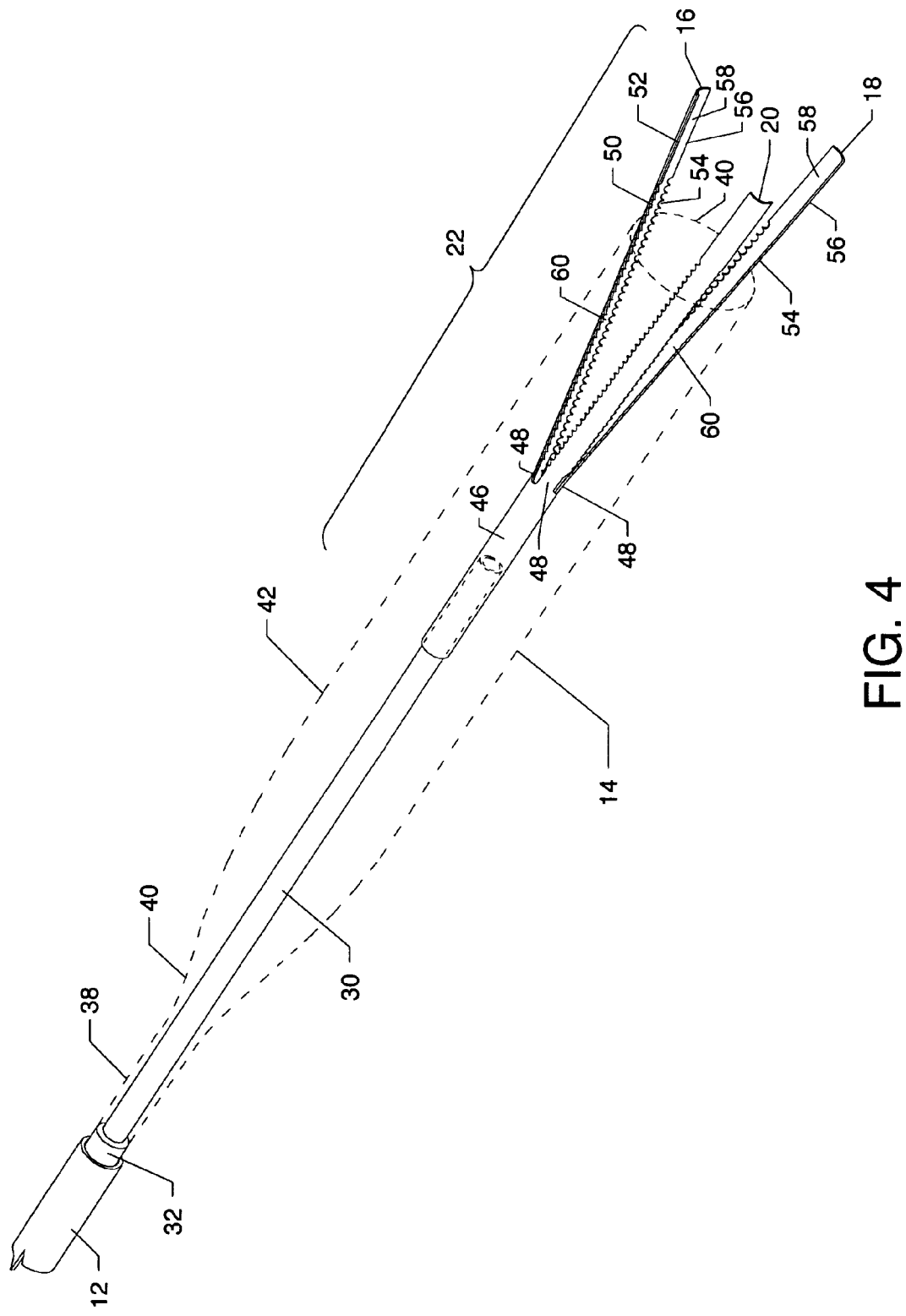
FIG. 4 is an assembled view of the components of FIG. 2.
Figure 5:
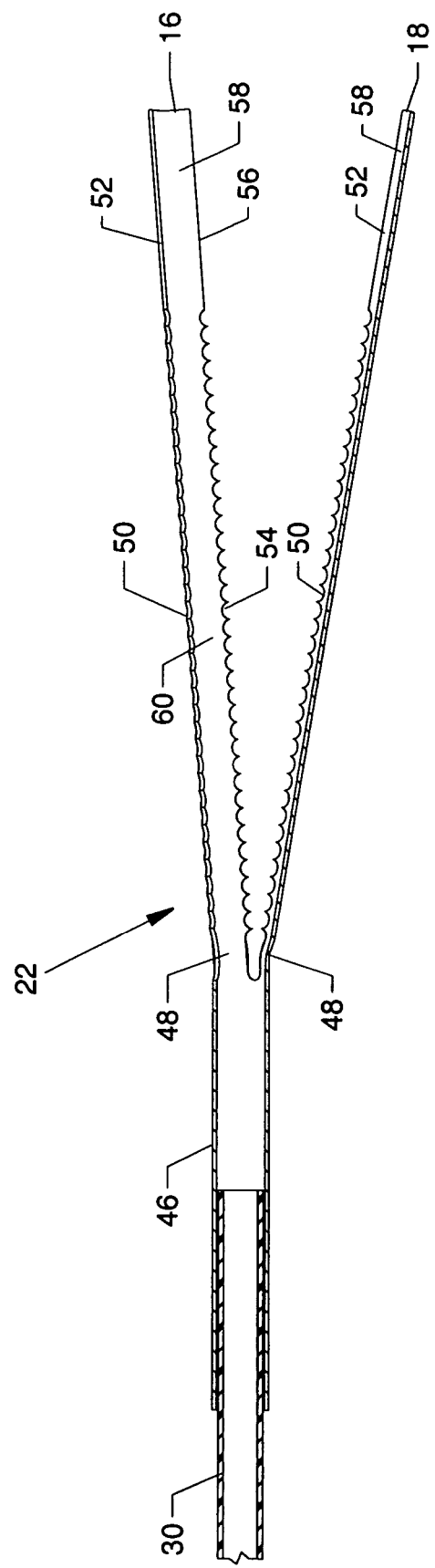
FIG. 5 is a cross section side view of a grasping mechanism.

FIG. 4 is an assembled view of the components of FIG. 2 showing the capture sleeve 14 in dashed lines, and FIG. 5 is a cross section side view of the grasping mechanism 22. In the illustration of FIG. 4, the capture/delivery sheath 12 is shown retracted from over the capture sleeve 14 in order to allow the outward expansion of the capture sleeve 14 into its memory or conformal shape. Shown, in particular, in FIGS. 4 and 5 is the one-piece grasping mechanism 22 which includes serrated fingers 16, 18 and 20, each of which extends distally from a tubular section 46 of the grasping mechanism 22. The serrated fingers 16, 18 and 20 of the one-piece grasping mechanism 22 are shown in the memory shape partially extending from the distal end of the capture sleeve 14. The distal end of the grasping mechanism positioning tube 30 is fitted within the interior of the tube section 46 and secured therein, such as by a weldment, an adhesive, or another suitable method. The serrated fingers 16, 18 and 20 can be arcuate in cross section or may be any other suitable profile. The similarly configured serrated fingers 16, 18 and 20 have like features including flexible joint sections 48 transitioning between the tubular section 46 and the serrated fingers 16, 18 and 20. Each of the similarly configured serrated fingers 16, 18 and 20 includes a serrated edge 50, an adjacent shorter smooth edge 52, an opposed serrated edge 54, and an adjacent shorter smooth edge 56, the fingers extending distally from the flexible joint sections 48. A smooth surface 58 is located between the opposed smooth edges 52 and 56, and an elongated smooth surface 60 is located between the serrated edges 50 and 54. The surfaces 58 and 60 are preferably smooth surfaces, but such surfaces could include multi-dimensional frictional surfaces for assistance in gripping, grasping or otherwise frictionally engaging an embolic thrombus, such as, but not limited to, surfaces having grooves, serrations, cross hatches, teeth, gritty surfaces, perforations, and the like. Although serrations are located along serrated edges 50 and 54 of the serrated fingers 16, 18 and 20, other configurations which could grasp, cut, tear, sever or otherwise act to separate embolic thrombus debris can also be used.

One method of forming the serrations would be to provide a series of closely spaced holes in end to end tangency or near tangent alignment and then cutting them with a laser or by slicing or otherwise providing for separation of the holes along the tangency or near tangency whereby the remaining semi-circles provide lines of opposing serrated edges. Although semi-circular serrations are shown, other geometric serration like configurations could include, but are not limited to, a saw tooth configuration, grooves, crosshatch surfaces, teeth, gritty surfaces, perforations and the like.

Figure 6:
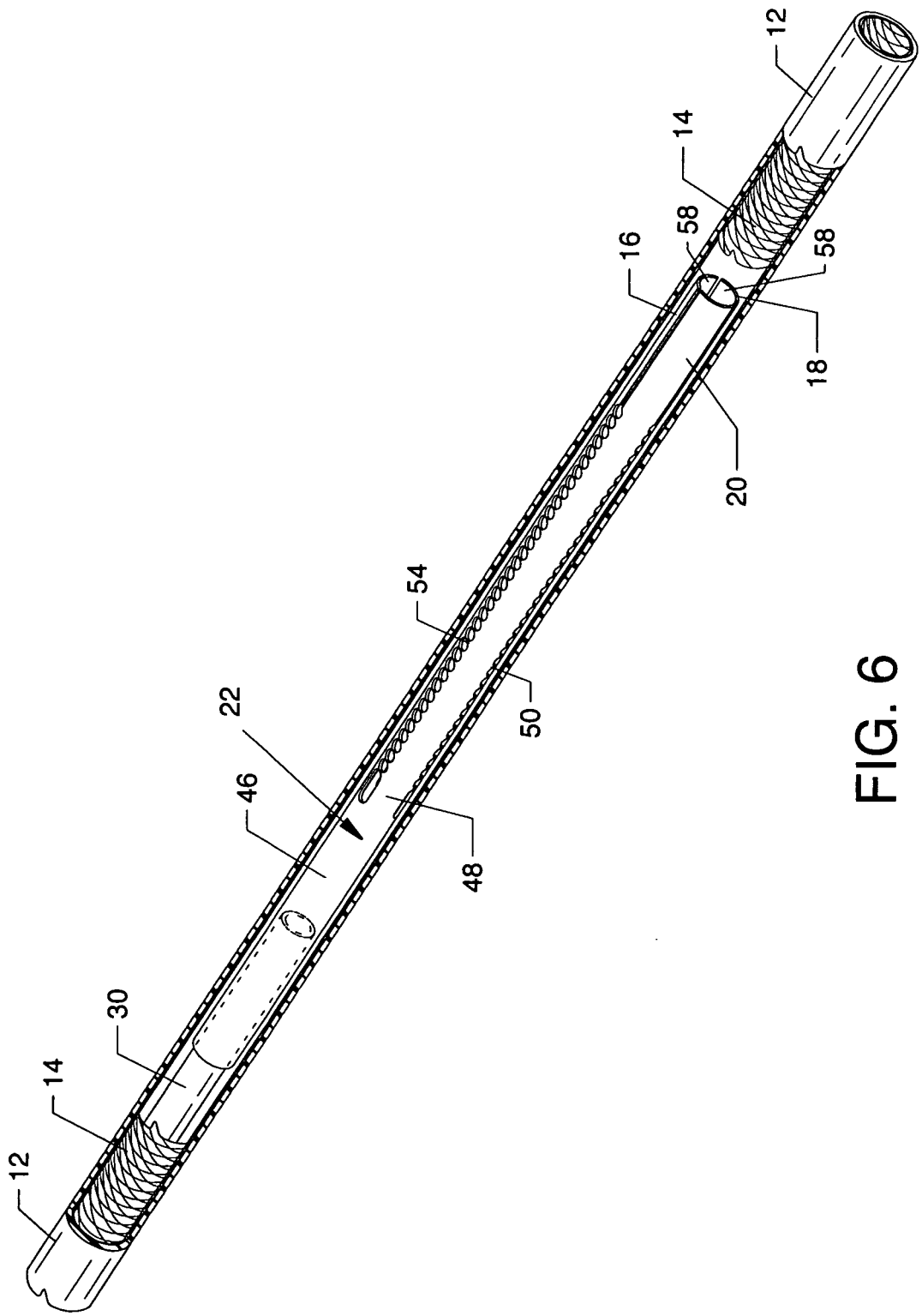
FIG. 6 is an isometric view in cutaway of the components of FIG. 2.

FIG. 6 is an isometric cutaway view of the components of FIG. 2 where the distal portion of the capture/delivery sheath 12 is shown over and about and compressing the capture sleeve 14 and the grasping mechanism 22. The relative positioning of the components, such as shown, is suitable for transitional use with a guidewire along the central tubular axis of such components. Especially noted is the compressed position of the arcuate serrated fingers 16, 18 and 20 of the grasping mechanism 22 which provides for a tubular passageway in combination with the tubular section 46 for direct guidewire passage therethrough. Such a guidewire can also pass directly through the grasping mechanism positioning tube 30 and indirectly through other closely associated components along the central tubular axis including the compressed capture sleeve 14, the capture sleeve positioning tube 32, and indirectly through the capture/delivery sheath operator 24, the capture sleeve operator 26, and the grasping mechanism operator 28.

Figure 7:
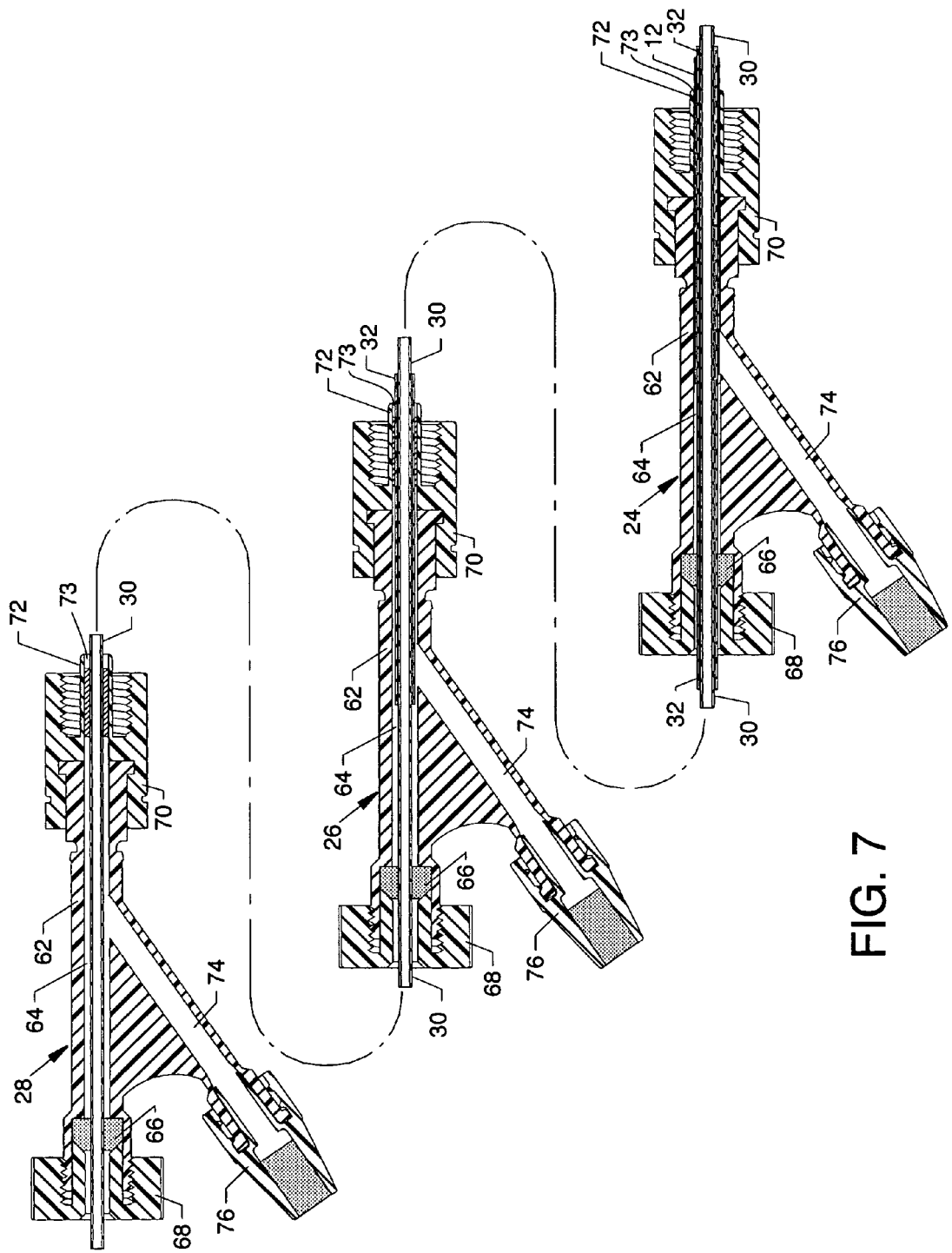
FIG. 7 is a segmented cross section view of the capture/delivery sheath operator, the capture sleeve operator, and the grasping mechanism operator, each in the form of a manifold.

FIG. 7 is a segmented cross section view of the capture/delivery sheath operator 24, the capture sleeve operator 26, and the grasping mechanism operator 28, each in the form of a manifold found commonly in the art. The capture/delivery sheath operator 24, the capture sleeve operator 26, and the grasping mechanism operator 28 are used in an end-to-end alignment, such as shown in FIG. 1, and are used to telescopingly position distally located components at the distal end of the invention using coaxially aligned tubular structures, the relationship of which is described with reference to FIG. 2. Briefly described, each operator includes a manifold body 62, a central passageway 64 extending along the manifold body 62, a seal 66, a hemostasis valve 68, a Luer connector 70, a tubular extension 72 (including a tubular passageway 73) extending through the Luer connector 70, a branch passageway 74, and a cap 76 which may be in the form of a Luer fitting.

The proximal end of the capture/delivery sheath 12 extends partially along the central passageway 64 of the capture/delivery sheath operator 24 and is positionally fixed therein by the use of an adhesive or another suitable method at the annular junction of the capture/delivery sheath 12 and the tubular extension 72 in the Luer connector 70 of the capture/delivery sheath operator 24. Generally, the capture/delivery sheath 12 can be positionably, telescopingly and variably aligned directly over and about portions of the capture sleeve positioning tube 32 and over and about the connected capture sleeve 14, and indirectly over and about portions of the grasping mechanism positioning tube 30 and over and about the connected distally located grasping mechanism 22.

The proximal end of the capture sleeve positioning tube 32 extends partially along the central passageway 64 of the capture sleeve operator 26 and is positionally fixed therein by the use of an adhesive or another suitable method at the annular junction of the capture sleeve positioning tube 32 and the tubular extension 72 in the Luer connector 70 of the capture sleeve operator 26. Additionally, the capture sleeve positioning tube 32 extends distally to enter the hemostasis valve 68, the seal 66 and the central passageway 64 of the capture/delivery sheath operator 24, and thence through the capture/delivery sheath 12 to connect to the distally located capture sleeve 14. The capture sleeve operator 26 can be used to slidingly position the capture sleeve positioning tube 32 (having the connected capture sleeve 14) along and within the capture/delivery sheath 12 in order to longitudinally position the capture sleeve 14 out of the influence of the capture/delivery sheath 12 or to return the capture sleeve 14 into the influence of the capture/delivery sheath 12. The seal 66 of the capture/delivery sheath operator 24 provides a slight pressure, which can easily be overcome, against the circumference of the capture sleeve positioning tube 32 in order to maintain the adjustable position of the capture sleeve positioning tube 32 with respect to the capture/delivery sheath operator 24 and to other associated telescopic components. Generally, the capture sleeve 14, connected to a capture sleeve positioning tube 32, can be positionably, telescopingly, and variably aligned directly over and about the grasping mechanism positioning tube 30 and connected grasping mechanism 22.

The proximal end of the grasping mechanism positioning tube 30 extends through the seal 66 and along the central passageway 64 of the grasping mechanism operator 28 and is positionally fixed therein by the use of adhesive or other suitable method at the annular junction of the grasping mechanism positioning tube 30 and the passageway 72 in the Luer connector 70 of the grasping mechanism operator 28. Additionally, the grasping mechanism positioning tube 30 extends distally to enter the hemostasis valve 68, the seal 66, and the central passageway 64 of the capture sleeve operator 26, and thence through the capture sleeve positioning tube 32 to connect to the distally located grasping mechanism 22. The grasping mechanism operator 28 can be used to slidingly position the grasping mechanism positioning tube 30 (connected to the grasping mechanism 22) along and within the capture sleeve positioning tube 32 in order to position the grasping mechanism 22 longitudinally with respect to the capture/delivery sheath 12 and the capture sleeve 14. The seal 66 of the capture sleeve operator 26 provides slight pressure, which can easily be overcome, against the circumference of the grasping mechanism positioning tube 30 in order to maintain the adjustable position of the grasping mechanism positioning tube 30 with respect to the capture sleeve operator 26 and to other associated telescopic components.

Figure 8:
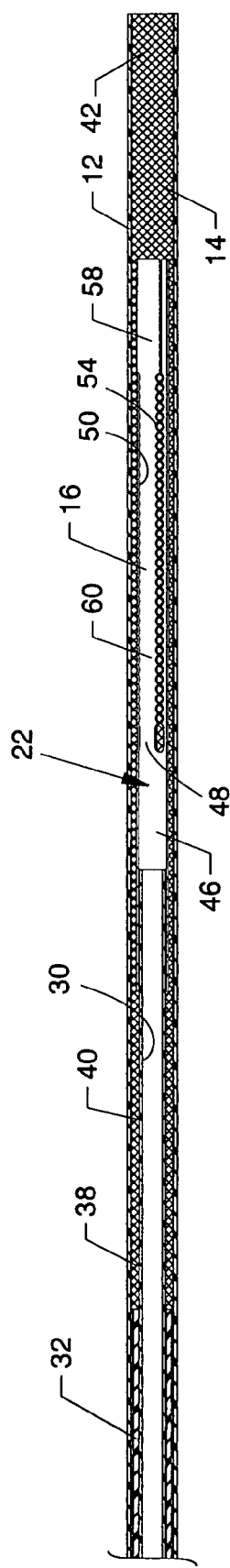
FIG. 8 is a partial cross section view of the distal end of the catheter for the removal of an organized embolic thrombus.

FIG. 8 is a partial cross section view of the distal end of the catheter 10 for the removal of an organized embolic thrombus showing the compression of the capture sleeve 14 and of the serrated fingers of the grasping mechanism 22 by the capture/delivery sheath 12 which surrounds them. It is noted that the interior regions of the assembled components provide unrestricted access for use with a guidewire.

Figure 9:
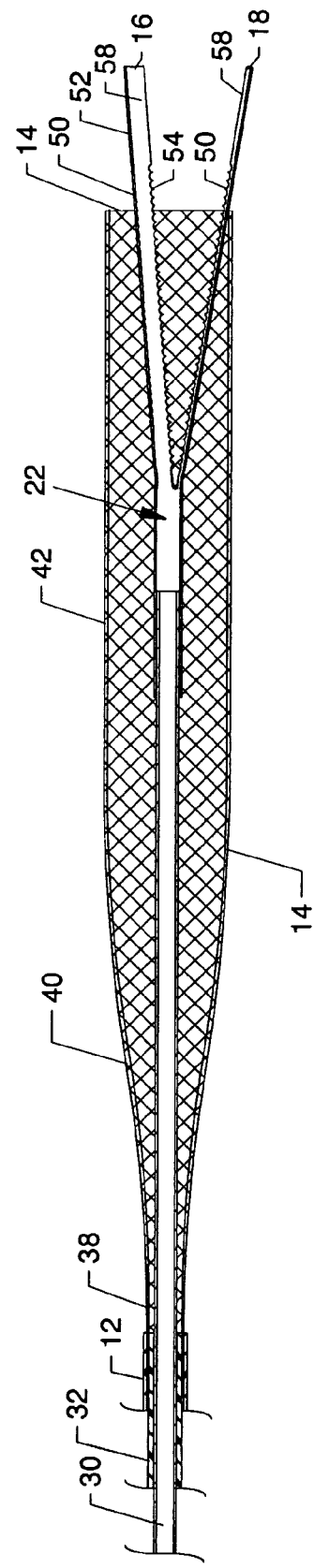
FIG. 9 is a cross section view in partial cutaway of the components of FIG. 8; and, FIGS. 10-15 are cross section side views illustrating the use of the invention for the removal of an embolic thrombus from a vessel.

FIG. 9 is a cross section view in partial cutaway of the components of FIG. 8 where the capture/delivery sheath 12 has been positioned proximally and where the grasping mechanism 22 has been positioned distally a short distance, but in partial alignment with the capture sleeve 14. When not under the influence of the capture/delivery sheath 12, the grasping mechanism 22 and the capture sleeve 14 expand outwardly toward their memory shape positions.

MODE OF OPERATION

The mode of operation of the catheter 10 for the removal of an organized embolic thrombus is described in steps in FIGS. 10-15, preferably with the use of a distal occlusion balloon guidewire 76 having at least an inflation tube 78 and an inflatable distal occlusion balloon 80, such as, but not limited to, that previously referenced in patent application Ser. No. 11/581,613, or with another suitable pulling device, such as by the present inventors or others. The invention is used in a telescopic fashion, whereby the capture/delivery sheath operator 24, the capture sleeve operator 26, and the grasping mechanism operator 28 can be appropriately spaced and positioned longitudinally with respect to each other in order to change, affix, adjust or otherwise suitably influence the positional relationship of the distally located components, such as the capture/delivery sheath 12, the capture sleeve 14, the grasping mechanism 22, and the distal occlusion balloon guidewire 76 with respect to each other, as well as the closely associated and corresponding grasping mechanism positioning tube 30 and the capture sleeve positioning tube 32. The distal occlusion balloon guidewire 76 is also positionable with respect to the catheter 10. The capture/delivery sheath operator 24, the capture sleeve operator 26, the grasping mechanism operator 28, and the distal occlusion balloon guidewire 76 can be operated independently one or more at a time in order to effect particular positional and functional relationships. The capture/delivery sheath operator 24, the capture sleeve operator 26, the grasping mechanism operator 28 associated with the capture/delivery sheath 12, the capture sleeve 14 and the grasping mechanism 22 and associated positioning tubes can, as well as the distal occlusion balloon guidewire 76, be operated individually or unitarily two or more at a time.

Figure 10:
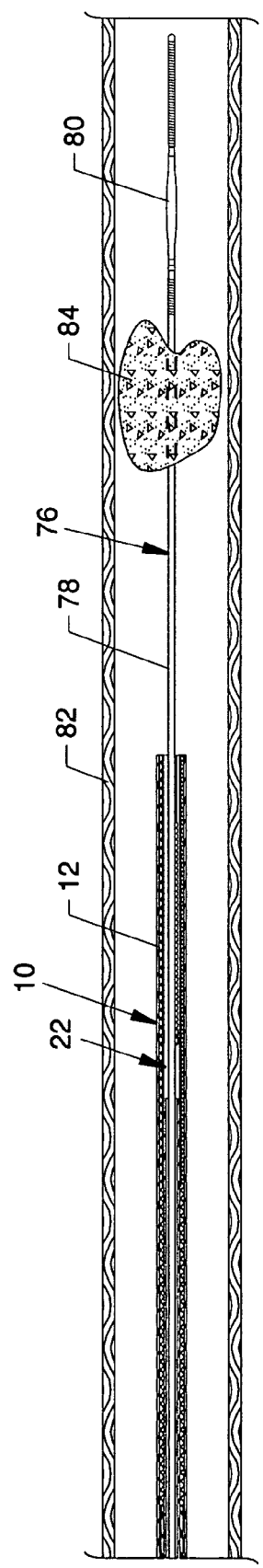

FIG. 10 is in general a cross section view (except for a the view of the distal portion of the suitable distal occlusion balloon guidewire 76) illustrating a step in the use of the catheter 10 with the distal occlusion balloon guidewire 76 where the distal tip of the guidewire 76 has been advanced through a blood vessel 82 and through the body of an embolic thrombus 84 located in the blood vessel 82 in order to position the occlusion balloon 80 a short distance distal to the embolic thrombus 84.

The other part of this step requires, preferably, that the capture/delivery sheath operator 24, the capture sleeve operator 26, and the grasping mechanism operator 28 first are individually positioned longitudinally with respect to each other to mutually align the capture sleeve 14, the grasping mechanism 22, and the distal end of the capture/delivery sheath 12 at the distal end of the catheter 10, as shown in FIG. 6, for accommodation by the distal occlusion balloon guidewire 76, whereby the catheter 10 can be positioned unitarily over and about the distal occlusion balloon guidewire 76. Subsequent to such mutual alignment, the distal end of the catheter 10 is introduced into the blood vessel 82 over and about the distal occlusion balloon guidewire 76 in order to position the distal end of the capture/delivery sheath 12 at a location proximal to and near the site of the embolic thrombus 84. The distal occlusion balloon guidewire 76 is slidingly accommodated, either directly or indirectly, within the coaxially aligned components including the tubular like center of the compressed and closely juxtaposed serrated fingers 16, 18 and 20 of the grasping mechanism 22, the tubular section 46 of the grasping mechanism 22, the compressed capture sleeve 14, the grasping mechanism positioning tube 30, and the capture sleeve positioning tube 32. The distal occlusion balloon guidewire 76 is also slidingly accommodated within the tubular extension 72 of the Luer connector 70, the central passageway 64, the seal 66, the hemostasis valve 68, and other components associated with each of the following components including the capture/delivery sheath operator 24, the capture sleeve operator 26, and the grasping mechanism operator 28 (FIG. 7).

Figure 11:
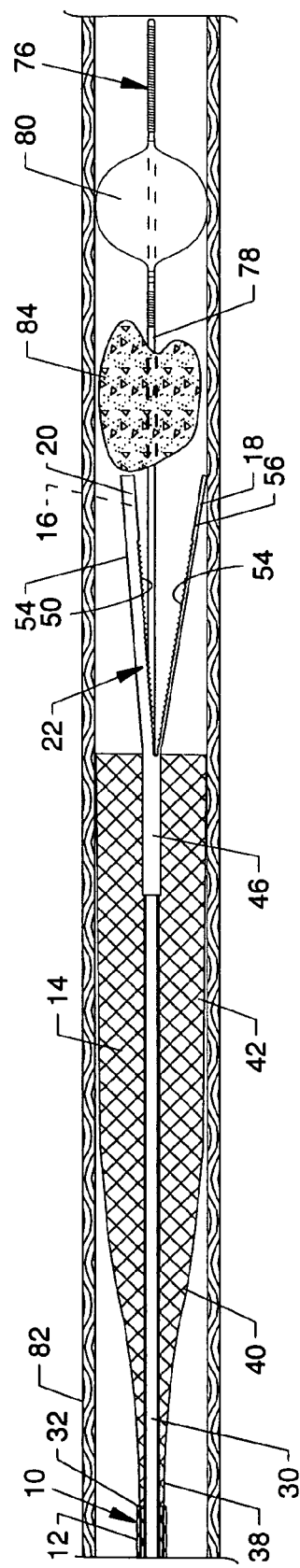

FIG. 11 illustrates a step where (1) the capture/delivery sheath operator 24 is positioned proximally to withdraw the distal portion of the capture/delivery sheath 12 from a compressive intimate contact with the capture sleeve 14 and from an indirect compressive transmitted contact with the serrated fingers 16, 18 and 20 of the grasping mechanism 22 in order to allow automatic expansion of the capture sleeve 14 and the serrated fingers 16, 18 and 20 to their conformal or memory shape; where (2) the grasping mechanism operator 28 is positioned distally to advance the grasping mechanism 22 distally to advance the serrated fingers 16, 18 and 20 partially or fully beyond the capture/delivery sheath 12; and where (3) the occlusion balloon 80 of the distal occlusion balloon guidewire 76 is inflated for the purpose of contacting and urging the embolic thrombus 84 in a proximal direction.

Figure 12:
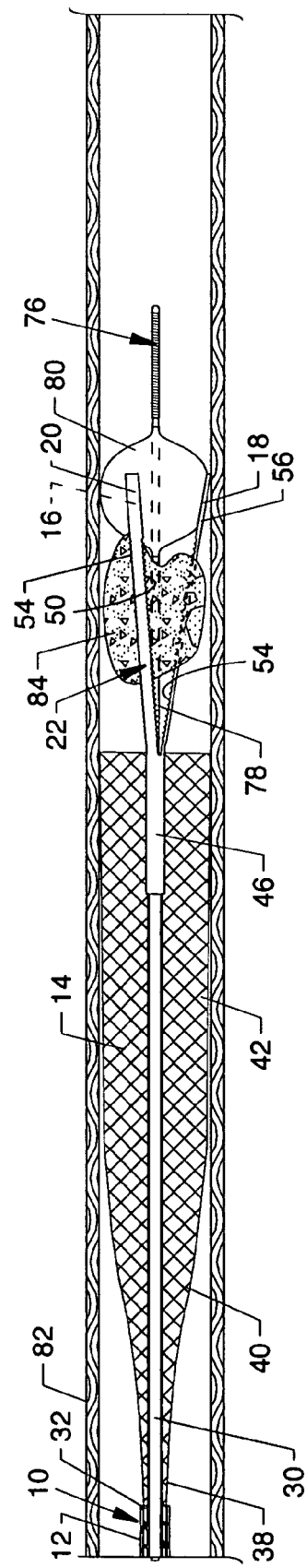

FIG. 12 illustrates a step where the distal occlusion balloon guidewire 76 has been positioned proximally, whereby the proximally moving inflated occlusion balloon 80 intimately contacts and urges the embolic thrombus 84 in a proximal direction, such that the embolic thrombus 84 engages the apex of the serrated fingers 16, 18 and 20 and features thereof. The process of such engagement of the embolic thrombus 80 involves the direct contact of the embolic thrombus 84 with the main structure of the serrated fingers 16, 18 and 20 including a momentary contact with smooth surfaces 58 and smooth edges 52 and 56 (FIG. 4) of the serrated fingers 16, 18 and 20 followed by a lasting contact with the smooth surfaces 60 and the serrated edges 50 and 54 (FIG. 4) of the serrated fingers 16, 18 and 20. Such engagement of the embolic thrombus 84 also involves an outward projection or reformation of the embolic thrombus 84 to extend between and outwardly from the spaces between the main structure of the serrated fingers 16, 18 and 20 including at least the serrated edges 50 and 54 of the serrated fingers 16, 18 and 20. Preferably, the inflated occlusion balloon 80 is moved proximally a suitable and appropriate distance to be brought into contact with the smooth surfaces 58 and the smooth edges 52 and 56 of the serrated fingers 16, 18 and 20, but not into contact with the serrated edges 50 and 54 of the serrated fingers 16, 18 and 20 in order to prevent an undesirable contacting of the inflated occlusion balloon 80 with the serrated edges 50 and 54, thus protecting the integrity of the occlusion balloon 80.

Figure 13:
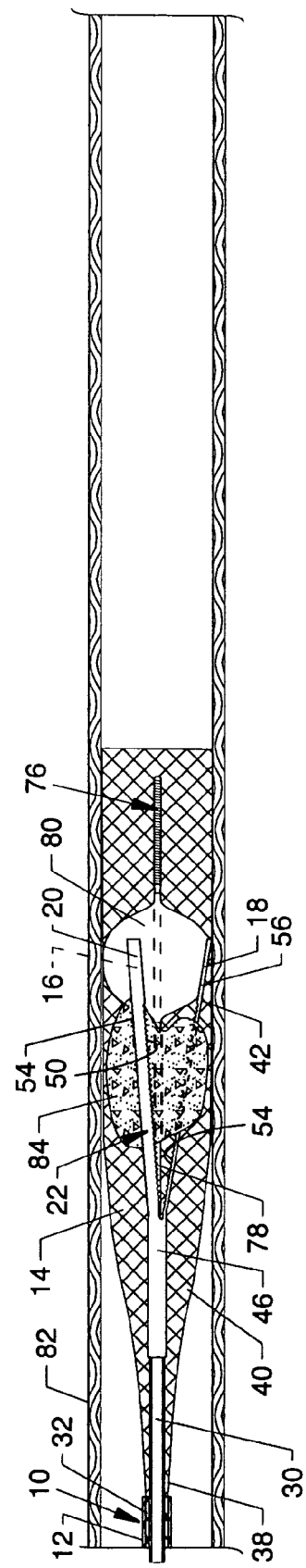

FIG. 13 illustrates a step where the grasping mechanism operator 28 and the distal balloon guidewire 76, including the inflated occlusion balloon 80, are unitarily positioned proximally, whereby the serrated fingers 16, 18 and 20 of the grasping mechanism 22, the inflated occlusion balloon 80 at the distal end of the distal balloon guidewire 76, the embolic thrombus 84 engaged between the serrated fingers 16, 18 and 20, and the inflated occlusion balloon 80 are all repositioned within the bounds of the capture sleeve 14.

Figure 14:
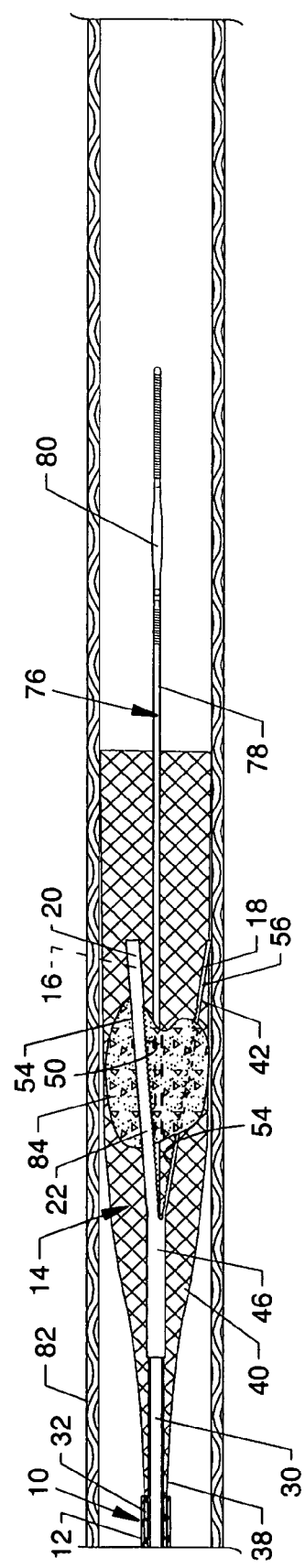

FIG. 14 illustrates a step where (1) the occlusion balloon 80 at the distal end the distal occlusion balloon guidewire 76 is deflated; and where (2) the distal occlusion balloon guidewire 76 including the deflated occlusion balloon 80 is repositioned distally a short distance to remove the deflated occlusion balloon 80 from the bounds of the capture sleeve 14; or (3) the distal occlusion balloon guidewire 76 including the deflated occlusion balloon 80 is removed distally and withdrawn from the catheter 10 to remove the deflated occlusion balloon 80 from the bounds of the capture sleeve 14.

Figure 15:
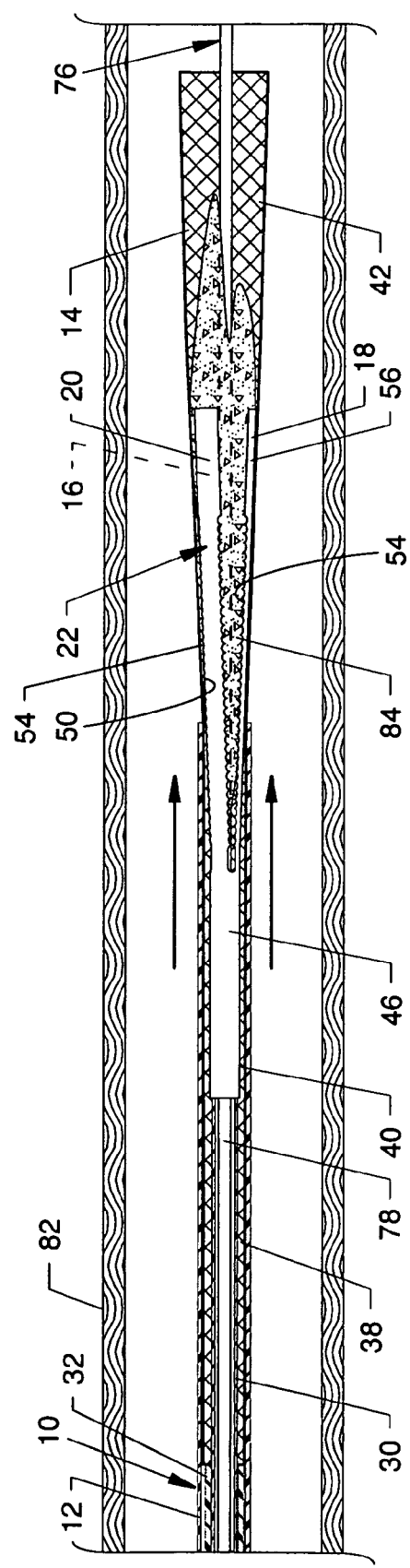

FIG. 15 illustrates simultaneous steps where (1) the capture/delivery sheath operator 24 is progressively positioned distally, whereby the capture/delivery sheath 12 progressively, directly, forcibly and slideably engages and compresses the capture sleeve 14; and where (2) the capture/delivery sheath operator 24 simultaneously, progressively, forcibly and indirectly communicates with and compresses the serrated fingers 16, 18 and 20 by a force transmitted through the intermediately located capture sleeve 14 to the serrated fingers 16, 18 and 20.

As the capture/delivery sheath 12 is advanced distally, the embolic thrombus 84 (debris) is squeezed and forced in an outward and distal direction past the serrated edges 50 and 54 of the progressively and continuously forced closing of the serrated fingers 16, 18 and 20. The serrated edges 50 and 54 help to tear and reduce the embolic thrombus 84 into smaller pieces as it is progressively and then finally contained within the serrated fingers 16, 18 and 20 and capture sleeve 14 when the capture/delivery sheath 12 is distally deployed fully thereover. Subsequent to the compressed capture of the embolic thrombus 84 by the grasping mechanism 22 and the capture sleeve 14, as previously described, the captured embolic thrombus 84 is removed proximally in another step when the grasping mechanism operator 28 and the capture sleeve operator 26 are simultaneously and unitarily removed proximally whereby the grasping mechanism positioning tube 30, the compressed associated grasping mechanism 22, the capture sleeve positioning tube 32 and the compressed associated capture sleeve 14 are all removed from the contact and influence of the capture/delivery sheath 12 and the associated capture/delivery sheath operator 24. Subsequent to such removal, the embolic thrombus 84 can be removed from the grasping mechanism 22. Another capture sleeve 14 and grasping mechanism 22 can be introduced or the same capture sleeve 14 and the grasping mechanism 22 can be cleaned and reintroduced into the blood vessel 82 via the capture/delivery sheath 12 and the distal occlusion balloon guidewire 76, if required.

Various modifications can be made to the present invention without departing from the apparent scope thereof.

CATHETER FOR REMOVAL OF AN ORGANIZED EMBOLIC THROMBUS

Parts List 10 catheter for removal of organized embolic thrombus
12 capture/delivery sheath
14 capture sleeve
16 serrated finger
18 serrated finger
20 serrated finger
22 grasping mechanism
24 capture/delivery sheath operator
26 capture sleeve operator
28 grasping mechanism operator
30 grasping mechanism positioning tube
32 capture sleeve positioning tube
34 nitinol strands
36 polymer strands
38 proximal section
40 flared section
42 distal section
44 annular edge
46 tubular section
48 flexible joint section
50 serrated edge
52 smooth edge
54 serrated edge
56 smooth edge
58 smooth surface
60 smooth surface
62 manifold body
64 central passageway
66 seal
68 hemostasis valve
70 Luer connector 72 tubular extension
73 tubular passageway
73 tubular passageway
74 branch passageway
76 distal occlusion balloon guidewire
78 inflation tube
80 occlusion balloon
82 blood vessel
84 embolic thrombus

The invention claimed is:

1. A catheter for removal of an embolic thrombus comprising:
   a capture sheath;
   a flexible capture sleeve having an expanded conformation and an unexpanded conformation;
   a grasping mechanism comprising plurality of flexible fingers and having an expanded conformation and an unexpanded conformation, said grasping mechanism attached to the distal end of a first elongated tube;
   an elongated guidewire having a proximal end and a distal end and having an occlusion balloon affixed to said elongated guidewire near said distal end, said elongated guidewire being slideable within said grasping mechanism such that said occlusion balloon is extendable distally beyond said grasping mechanism;
   wherein said capture sheath, said flexible capture sleeve, said grasping mechanism and said elongated guidewire form a telescopic system; and
   wherein said grasping mechanism, in said unexpanded conformation, defines a passageway to and through said first elongated tube; and
   wherein at least one of said plurality of flexible fingers includes a serrated edge, an adjacent shorter smooth edge, an opposed serrated edge, and an adjacent opposed shorter smooth edge, wherein an elongated smooth surface is located between said opposed serrated edges and, and an elongated smooth surface is located between said opposed smooth edges.

2. The catheter of claim 1, wherein said grasping mechanism is slideable within said flexible capture sleeve and said flexible capture sleeve is slideable within said capture sheath.

3. The catheter of claim 2, said capture sheath, said flexible capture sleeve, and said grasping mechanism are selectively telescopic.

4. The catheter of claim 1, wherein said plurality of flexible fingers, in said expanded conformation, are spaced apart a maximum amount at a distal end.

5. The catheter of claim 1, wherein each of said plurality of flexible fingers is straight when grasping mechanism is in said expanded conformation.

6. The catheter of claim 5, wherein each of said flexible fingers has an arced cross-section.

7. The catheter of claim 1, wherein said grasping mechanism in an expanded conformation tapers in a distal to proximal direction.

8. The catheter of claim 1, wherein said grasping mechanism is made from nitinol or heat treated stainless steel.

9. The catheter of claim 1, wherein said flexible capture sleeve is attached to a distal end of a second elongated tube.

10. The catheter of claim 9, wherein said flexible capture sleeve is a woven mesh of nitinol strands and polymer strands.

11. The catheter of claim 9, wherein said flexible capture sleeve has an expanded memory shape.

12. The catheter of claim 1, wherein said flexible capture sleeve and said grasping mechanism are in said expanded conformation when said capture sheath does not surround said plurality of flexible fingers and said flexible capture sleeve.

13. The catheter of claim 1, wherein said flexible capture sleeve and said grasping mechanism are in said unexpanded conformation when said capture sheath surrounds said grasping mechanism and said flexible capture sleeve.

14. The catheter of claim 1, wherein said occlusion balloon can be retracted into said flexible capture sleeve.

15. The catheter of claim 1 wherein said occlusion balloon can be retracted into a distal opening of said grasping mechanism in said unexpanded position.

16. A method for removal of an embolic thrombus from within a blood vessel comprising the steps of:
   a.) providing an elongated catheter with a grasping mechanism at its distal end, wherein, said grasping mechanism is attached to the distal end of a first elongated tube, and wherein an elongated guidewire having a proximal end and a distal end and having an occlusion balloon affixed to said elongated guidewire near said distal end, said elongated guidewire being slideable within said first elongated tube such that said occlusion balloon is extendable distally beyond said grasping mechanism, and wherein said grasping mechanism, in said unexpanded conformation, defines a passageway to and through said first elongated tube, and wherein said grasping mechanism comprises a plurality of flexible fingers, wherein at least one of said plurality of flexible fingers includes a serrated edge, an adjacent shorter smooth edge, an opposed serrated edge, and an adjacent opposed shorter smooth edge, wherein an elongated smooth surface is located between said opposed serrated edges and, and an elongated smooth surface is located between said opposed smooth edges;
   b.) inserting said distal end of said elongated catheter into said blood vessel in proximity to said embolic thrombus;
   c.) collapsing around at least a portion of said embolic thrombus with said plurality of flexible fingers and reducing said embolic thrombus; and
   d.) removing said grasping mechanism and at least a portion of said embolic thrombus from said blood vessel.

17. The method of claim 16, wherein said grasping mechanism has an expanded conformation and an unexpanded conformation and wherein said plurality of flexible fingers collapses around at least a portion of said embolic thrombus when said grasping mechanism moves from an expanded conformation to an unexpanded conformation.

18. The method of claim 17, wherein said opposed smooth edges are configured at a distal portion of each of said plurality of fingers.

19. The method of claim 16, further comprising the steps of providing and inflating an occlusion balloon distal to said embolic thrombus and retracting said occlusion balloon in a proximal direction such that said inflated occlusion balloon contacts and forces said embolic thrombus into said grasping mechanism and at least a portion of said occlusion balloon is retracted into a distal opening of said grasping mechanism.

20. The method of claim 19, further comprising the steps of providing a flexible capture sleeve proximal to embolic thrombus, wherein said flexible capture sleeve has an expanded conformation and an unexpanded conformation, and retracting said occlusion balloon, said embolic thrombus, and said grasping mechanism in a proximal direction into said flexible capture sleeve in said expanded conformation.

21. The method of claim 20, further comprising the steps of deflating said occlusion balloon; withdrawing said occlusion balloon entirely from said blood vessel; and finally, withdrawing said grasping mechanism and said flexible capture sleeve with said captured embolic thrombus entirely from said blood vessel.

* * * * *